US010458039B2

(12) United States Patent
Han et al.

(10) Patent No.: US 10,458,039 B2
(45) Date of Patent: Oct. 29, 2019

(54) ASYMMETRIC MONOMETALLIC NANOROD NANOPARTICLE DIMER AND RELATED COMPOSITIONS AND METHODS

(71) Applicant: KING ABDULLAH UNIVERSITY OF SCIENCE AND TECHNOLOGY, Thuwal (SA)

(72) Inventors: Yu Han, Thuwal (SA); Jianfeng Huang, Thuwal (SA); Yihan Zhu, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 203 days.

(21) Appl. No.: 15/513,257

(22) PCT Filed: Sep. 25, 2015

(86) PCT No.: PCT/IB2015/002077
§ 371 (c)(1),
(2) Date: Mar. 22, 2017

(87) PCT Pub. No.: WO2016/046645
PCT Pub. Date: Mar. 31, 2016

(65) Prior Publication Data
US 2017/0306520 A1    Oct. 26, 2017

Related U.S. Application Data

(60) Provisional application No. 62/055,369, filed on Sep. 25, 2014.

(51) Int. Cl.
*C30B 7/14*     (2006.01)
*B82Y 30/00*    (2011.01)
(Continued)

(52) U.S. Cl.
CPC ............... *C30B 7/14* (2013.01); *B82Y 30/00* (2013.01); *C03B 29/02* (2013.01); *C30B 29/02* (2013.01);
(Continued)

(58) Field of Classification Search
CPC ......... B82Y 30/00; B82Y 40/00; C30B 29/02; C30B 29/60; C30B 7/14
See application file for complete search history.

(56) References Cited

U.S. PATENT DOCUMENTS

2011/0274913 A1    11/2011  Lin et al.
2014/0077121 A1*    3/2014  Sun .................... H01F 1/0054
                                                    252/62.55

OTHER PUBLICATIONS

International Search Report and Written Opinion received in connection with international application No. PCT/IB2015/002077; dated Mar. 1, 2016.
(Continued)

Primary Examiner — Matthew J Song
(74) Attorney, Agent, or Firm — Pabst Patent Group LLP

(57) ABSTRACT

The fabrication of asymmetric monometallic nanocrystals with novel properties for plasmonics, nanophotonics and nanoelectronics. Asymmetric monometallic plasmonic nanocrystals are of both fundamental synthetic challenge and practical significance. In an example, a thiol-ligand mediated growth strategy that enables the synthesis of unprecedented Au Nanorod-Au Nanoparticle (AuNR-AuNP) dimers from pre-synthesized AuNR seeds. Using high-resolution electron microscopy and tomography, crystal structure and three-dimensional morphology of the dimer, as well as the growth pathway of the AuNP on the AuNR seed, was investigated for this example. The dimer exhibits an extraordinary broadband optical extinction spectrum spanning the UV, visible, and near infrared regions (300-1300 nm). This unexpected property makes the AuNR-
(Continued)

TEM images of (a) the AuNR seeds and (b-d) various Au nanostructures after seeded growth with different concentrations of 4-MP: (b) peanut-shaped AuNRs (4-MP: 0 mM), (c) irregular rugged AuNRs (4-MP: 1 mM), and (d) AuNR-AuNP dimers (4-MP: 10 mM).

AuNP dimer example useful for many nanophotonic applications. In two experiments, the dimer example was tested as a surface-enhanced Raman scattering (SERS) substrate and a solar light harvester for photothermal conversion, in comparison with the mixture of AuNR and AuNP. In the SERS experiment, the dimer example showed an enhancement factor about 10 times higher than that of the mixture, when the excitation wavelength (660 nm) was off the two surface plasmon resonance (SPR) bands of the mixture. In the photothermal conversion experiment under simulated sunlight illumination, the dimer example exhibited an energy conversion efficiency about 1.4 times as high as that of the mixture.

17 Claims, 9 Drawing Sheets

(51) Int. Cl.
    C30B 29/02    (2006.01)
    C30B 29/60    (2006.01)
    G01N 21/65    (2006.01)
    C03B 29/02    (2006.01)
    B82Y 40/00    (2011.01)

(52) U.S. Cl.
    CPC ........... *C30B 29/60* (2013.01); *G01N 21/658* (2013.01); *B82Y 40/00* (2013.01)

(56) References Cited

OTHER PUBLICATIONS

Bidault et al., "Plasmon-Based Nanolenses Assembled on a Well-Defined DNA Template", *J. Am. Chem. Soc.* 2008, 130, 2750.
Brandi et al., "General-stacking-fault energies in highly strained metallic environments: Ab initio calculations", *Phys. Rev. B* 2007, 76, 054124.
Branicio et al., "Effect of strain on the stacking fault energy of copper: A first-principles study", *Phys. Rev. B* 2013, 88, 064104.
Busson et al.,"Optical and Topological Characterization of Gold Nanoparticle Dimers Linked by a Single DNA Double Strand", *Nano Lett.* 2011, 11, 5060.
Carbó-Argibay et al., "The Crystalline Structure of Gold Nanorods Revisited: Evidence for Higher-Index Lateral Facets", Angew. Chem. Int. Ed. 2010, 49, 9397.
Carbone et al., "Colloidal heterostructured nanocrystals: Synthesis and growth mechanisms", Nano Today 2010, 5, 449.
Chen et al., "Measuring Ensemble-Averaged Surface-Enhanced Raman Scattering in the Hotspots of Colloidal Nanoparticle Dimers and Trimers", J. Am. Chem. Soc. 2010, 132, 3644.
Chen et al., "Shape- and Size-Dependent Refractive Index Sensitivity of Gold Nanoparticles", Langmuir 2008, 24, 5233.
Cheng et al., "Gold Nanoparticle Dimers for Plasmon Sensing", Langmuir 2011, 27, 7884.
Fang et al., "Evolution of Light-Induced Vapor Generation at a Liquid-Immersed Metallic Nanoparticle", Nano Lett. 2013, 13, 1736.
Faust et al., "The Growth of Semiconductor Crystals from Solution Using the Twin-Plane Reentrant-Edge Mechanism", J. Phys. Chem. Solids 1964, 25, 1407.
Feng et al., "An Unconventional Role of Ligand in Continuously Tuning of Metal-Metal Interfacial Strain", J. Am. Chem. Soc. 2012, 134, 2004.
Gao et al., "Semiclassical approach to plasmon-electron coupling and Landau damping of surface Plasmons", J. Chem. Phys. 2011, 134, 134702.
Gole et al., "Seed-Mediated Synthesis of Gold Nanorods: Role of the Size and Nature of the Seed", J. Chem. Mater. 2004, 16, 3633.

Goris et al. , "Atomic-scale determination of surface facets in gold nanorods",Nat. Mater. 2012. 11, 930.
Huang et al., "Site-Specific Growth of Au—Pd Alloy Horns on Au Nanorods: A Platform for Highly Sensitive Monitoring of Catalytic Reactions by Surface Enhancement Raman Spectroscopy", J. Am. Chem. Soc. 2013, 135, 8552.
Huang, F.and Baumberg, J., "Actively Tuned Plasmons on Elastomerically Driven Au Nanoparticle Dimers", J. Nano Lett. 2010, 10, 1787.
Hÿtch et al., "Quantitative measurement of displacement and strain fields from HREM micrographs", Ultramicroscopy 1998, 74, 131.
Jahnátek et al., "Shear deformation, ideal strength, and stacking fault formation of fcc metals: A density-functional study of Al and Cu", Rev. B 2009, 79, 224103.
Jana et al., "Evidence for Seed-Mediated Nucleation in the Chemical Reduction of Gold Salts to Gold Nanoparticles", Chem. Mater. 2001, 13, 2313.
Ji et al., "High purity gold nanocrystal dimmers: scalable synthesis and size-dependent plasmonic and Raman enhancement" Chem. Sci., 2014, 5, 311.
Katz-Boon et al., "Three-Dimensional Morphology and Crystallography of Gold Nanorods" J. Nano Lett. 2011, 11, 273.
Kleinman et al., "Structure Enhancement Factor Relationships in Single Gold Nanoantennas by Surface-Enhanced Raman Excitation Spectroscopy", J. Am. Chem. Soc. 2013, 135, 301.
Kumar et al., "Surface Plasmon coupling in end-to-end linked gold nanorod dimmers and trimers", Phys. Chem. Chem. Phys. 2013, vol. 15, 4258.
Lee et al., "Universal Sulfide-Assisted Synthesis of M—Ag Heterodimers (M=Pd, Au, Pt) as Efficient Platforms for Fabricating Metal-Semiconductor Heteronanostructures", J. Am. Chem. Soc. 2014, 136, 5221.
Lee et al., "Directional Synthesis and Assembly of Bimetallic Nanosnowmen with DNA", J. Am. Chem. Soc. 2012, 134, 5456.
Leonhardt, "Optical Conformal Mapping", U. Science 2006, 312, 1777.
Li et al., "Etching and Dimerization: A Simple and Versatile Route to Dimers of Silver Nanospheres with a Range of Sizes", Angew. Chem. Int. Ed. 2010, 49, 164.
Li et al., "Dimers of Silver Nanospheres: Facile Synthesis and Their Use as Hot Spots for Surface-Enhanced Raman Scattering", Nano Lett. 2009, 9, 485. Downloaded from https://www.ncbi.nlm.nih.gov/pmc/articles/PMC2629641/.
Lim et al., "Highly uniform and reproducible surface-enhanced Raman scattering from DNA-tailorable nanoparticles with 1-nm interior gap", Nat. Nanotechnol. 2011, 6, 452.
Liu et al., "In situ tracing of atom migration in Pt/NiPt hollow spheres during catalysis of Co oxidation", Chem. Commun. 2014, 50, 1804.
Lombardi et al.,"Optical Response of Individual Au_Ag@SiO2 Heterodimers", ACS Nano, 2013, 7, 2522.
McMahon et al., "Gold nanoparticle dimer plasmonics: finite element method calculations of the electromagnetic enhancement to surface-enhanced Raman spectroscopy", Anal. Bioanal. Chem. 2009, 394, 1819.
Neumann et al., "Solar Vapor Generation Enabled by Nanoparticles", ACS Nano, 2013, 7, 42.
Ni et al., "Tailoring Longitudinal Surface Plasmon Wavelengths, Scattering and Absorption Cross Sections of Gold Nanorods", ACS Nano, 2008, 2, 677.
Paine et al., "Strain Relief in Compositionally Graded $Si_{1-x}Ge_x$ Formed by High Dose Ion Implantation", J. Electron. Mater. 1991, 20, 735.
Pendry et al., "Controlling Electromagnetic Fields", Science 2006, 312, 1780.
Peng et al., "Designer platinum nanoparticles: Control of shape, composition in alloy, nanostructure and electrocatalytic property", Nano Today 2009, 4, 143.
Polman, A., "Solar Steam Nanobubbles", ACS nano 2013, 7, 15.
Ringler et al., "Moving Nanoparticles with Raman Scattering" Nano Lett. 2007, 7, 2753.
Sardar, et al., "Versatile Solid Phase Synthesis of Gold Nanoparticle Dimers Using an Asymmetric Functionalization Approach", J. Am. Chem. Soc. 2007, 129, 5356.

(56) References Cited

OTHER PUBLICATIONS

Sau et al., "Room Temperature, High-Yield Synthesis of Multiple Shapes of Gold Nanoparticles in Aqueous Solution", J. Am. Chem. Soc. 2004, 126, 8648.
Shao et al., "Angle- and Energy-Resolved Plasmon Coupling in Gold Nanorod Dimers", ACS Nano, 2010, vol. 4(6), 3053-3062.
Sohn et al., "Construction of Evolutionary Tree for Morphological Engineering of Nanoparticles", ACS Nano 2009, 3, 2191.
Wang et al., "Polymer-Encapsulated Gold-Nanoparticle Dimers: Facile Preparation and Catalytical Application in Guided Growth of Dimeric ZnO-Nanowires", Nano Lett. 2008, 8, 2643.
Watari et al., "Differential stress induced by thiol adsorption on facetted nanocrystals", Nat. Mater. 2011, 10, 862.
Yim, T. J.; Wang, Y.; Zhang, X., "Synthesis of a gold nanoparticle dimer plasmonic resonator through two-phase-mediated functionalization" Nanotechnology 2008, 19, 435605.
Yuan et al., "Balancing the Rate of Cluster Growth and Etching for Gram-Scale Synthesis of Thiolate-Protected Au25 Nanoclusters with Atomic Precision", Angew. Chem. Int. Ed. 2014, 53, 4623.
Zeng et al., "Colloidal Hybrid Nanocrystals: Synthesis, Properties, and Perspectives", Nanocrystal (Chapter 3); Publisher: InTech, 2011.
Zeng et al., "Controlling the Nucleation and Growth of Silver on Palladium Nanocubes by Manipulating the Reaction Kinetics", Angew. Chem. Int. Ed. 2012, 51, 2354.
Zhu et al., "Kinetically Controlled Overgrowth of Ag or Au on Pd Nanocrystal Seeds: From Hybrid Dimers to Nonconcentric and Concentric Bimetallic Nanocrystals", J. Am. Chem. Soc. 2012, 134, 15822.
Zhu et al., "Developing Mutually Encapsulating Materials for Versatile Syntheses of Multilayer Metal—Silica—Polymer Hybrid Nanostructures", Small 2012, 8, 1857.
Gleiter et al., "The Stacking Fault Energy in the Vicinity of a Coherent Twin Boundary", *Philos. Mag.* 1973, 27, 1009.
H. Hofmeister et al., "Multiple Twinniing in the Solid Phase Crystallization of Amorphous Germanium", J. *Mater. Sci. Forum* 1993, 113-115, 631.

\* cited by examiner

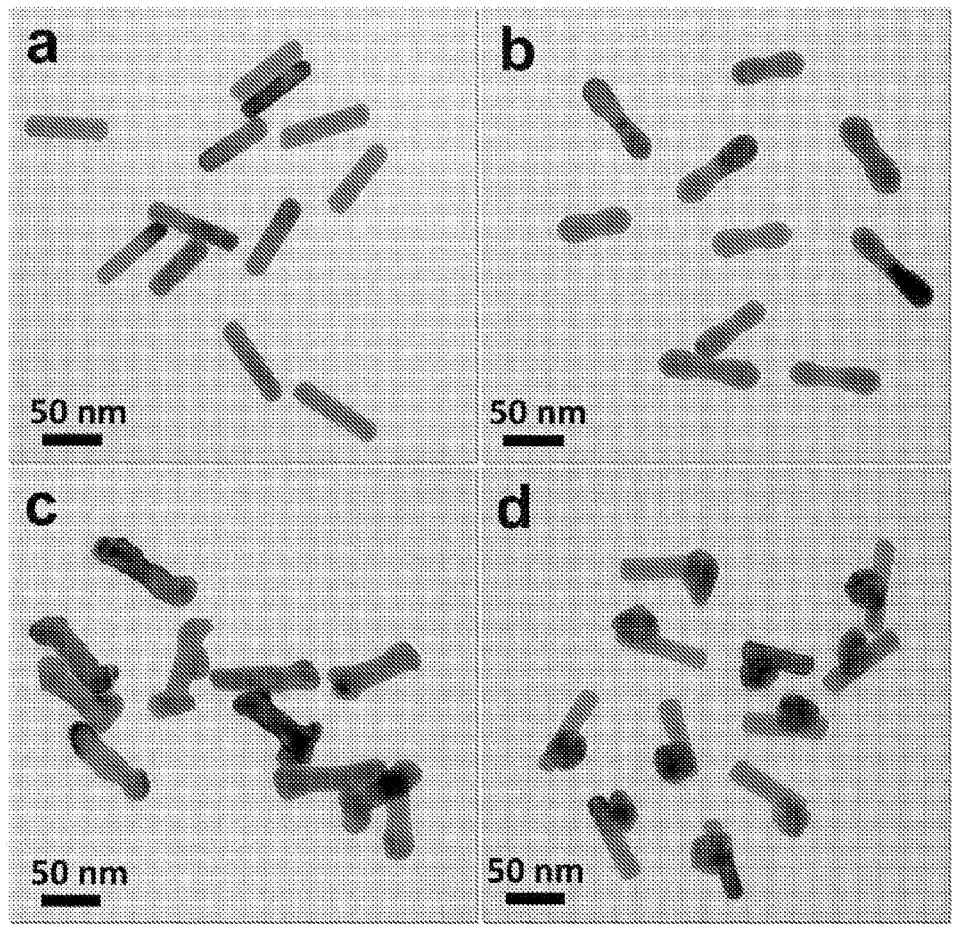
Figure 1. TEM images of (a) the AuNR seeds and (b-d) various Au nanostructures after seeded growth with different concentrations of 4-MP: (b) peanut-shaped AuNRs (4-MP: 0 mM), (c) irregular rugged AuNRs (4-MP: 1 mM), and (d) AuNR-AuNP dimers (4-MP: 10 mM).

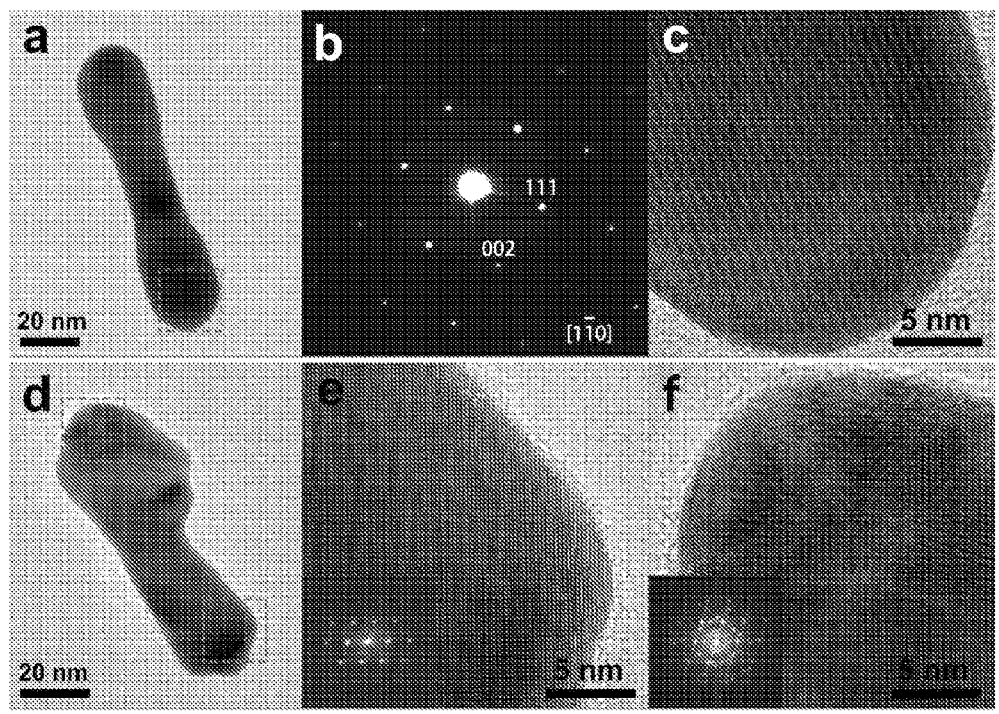

Figure 2. (a) TEM image and (b) indexed SAED pattern of a single-crystalline peanut-shaped AuNR taken along the [1$\bar{1}$0] axis; (c) HRTEM image of the highlighted region in (a). (d) TEM image of an irregular rugged AuNR, which contains both epitaxially grown (single-crystalline) and multiple twinned domains, as indicated by the HRTEM images (e and f) and the corresponding FFT diffractograms (insets) taken from the two highlighted regions in (d).

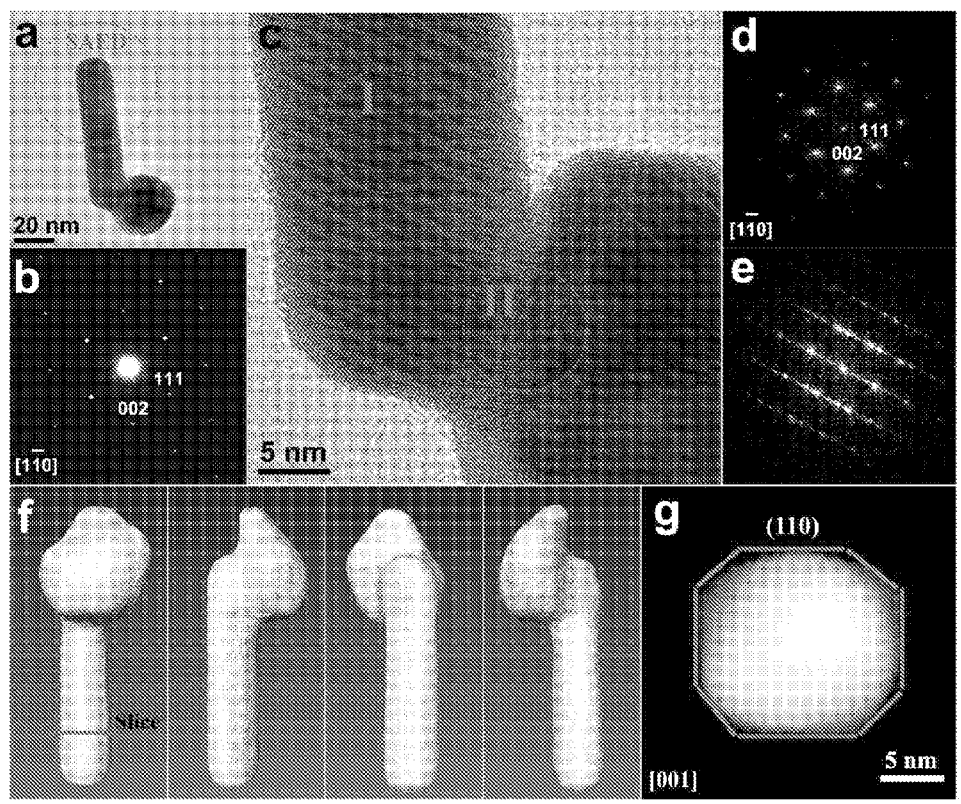

Figure 3. (a) TEM image a AuNR-AuNP dimer taken along the [1$\bar{1}$0] direction of the AuNR. (b) SAED pattern taken from the marked region in (a), illustrating the single-crystalline nature of AuNR in the dimer. (c) HRTEM image of the AuNR-AuNP dimer, showing single-crystalline AuNR, multiple twinned AuNP, and a stacking fault-rich interface. (d, e) FFT diffractograms of (d) region I and (e) region II marked in (c). (f) Reconstructed tomographic images of a AuNR-AuNP dimer crystal projected along four <110> directions of the AuNR. (g) A tomographic cross-section slice of the AuNR in the dimer along the [001] axis, as illustrated in (f).

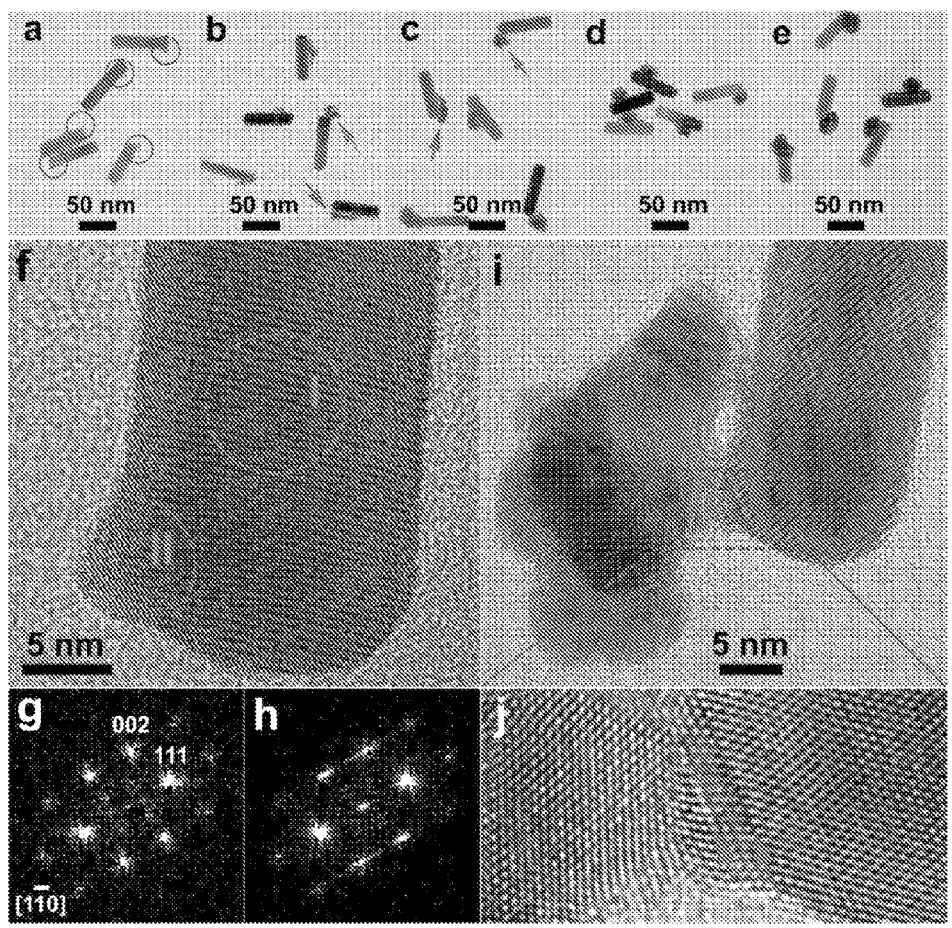

Figure 4. TEM images of various intermediates of the AuNR-AuNP dimer at different seeded growth stages, which were obtained by quenching the reaction at (a) 3, (b) 10, (c) 20, (d) 60, and (e) 180 s. The circles in (a) indicate the tiny budding particles. The arrows in (b and c) indicate worm-like agglomerates (red arrows) and cauliflower-like agglomerates (green arrows). (f) HRTEM image of the intermediate at 3 s taken along the [1$\bar{1}$0] axis of the AuNR, showing a small particle protruding from the AuNR along the [111] direction. (g, h) FFT diffractograms of (g) region I and (h) region II marked in (f). The diffuse reflections in (h) are indicative of the presence of stacking faults. (i) HRTEM image of the intermediate at 20 s taken along the [1$\bar{1}$0] axis of the AuNR. The ellipse indicates a gap formed by the cauliflower-like agglomerate and the AuNR. (j) Enlarged HRTEM image of the interface region marked in (i), in which two arrows indicate nanotwin boundaries.

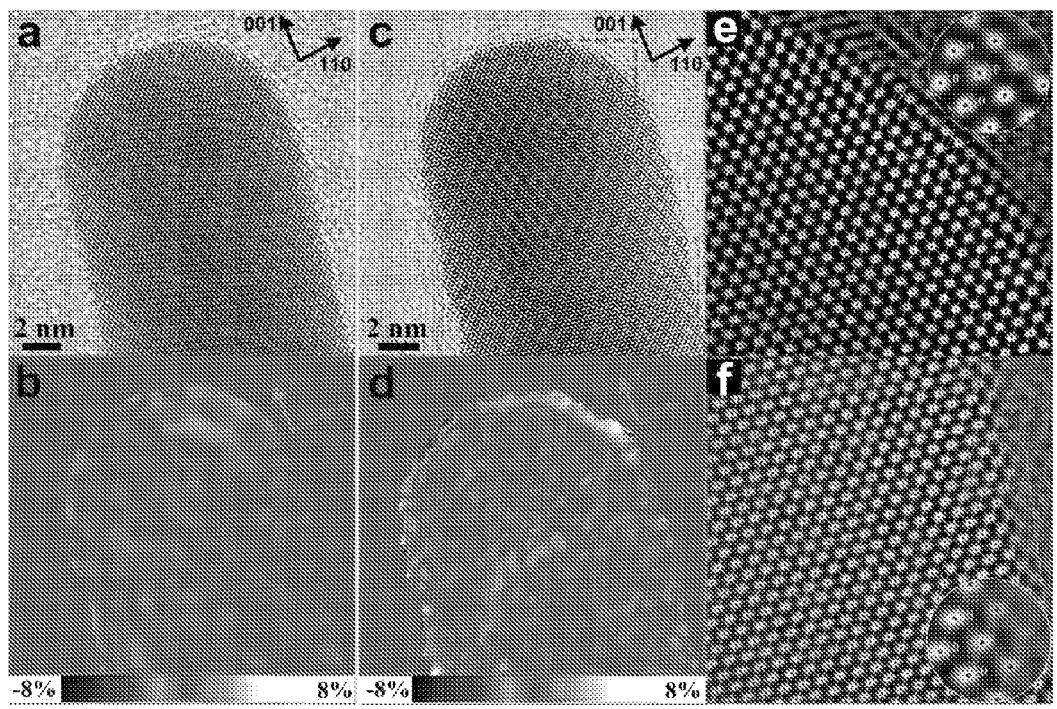

Figure 5. (a, c) Atomic-resolution HRTEM images of (a) the as-synthesized (CTAB capped) AuNR and (c) 4-MP incubated AuNR taken along the $[1\bar{1}0]$ axes. (b, d) corresponding strain distributions of the shear component ($\varepsilon_{xy}$, the magnitude cut-off is ± 8%) determined by geometric phase analysis. (e, f) Enlarged Bragg-filtered HRTEM images of (f) region I and (e) region II, as marked in (c). The maxima of atomic columns are connected to form an array of rhombuses, where the resulting obtuse angles (θ) correlate with the magnitudes of the strains.

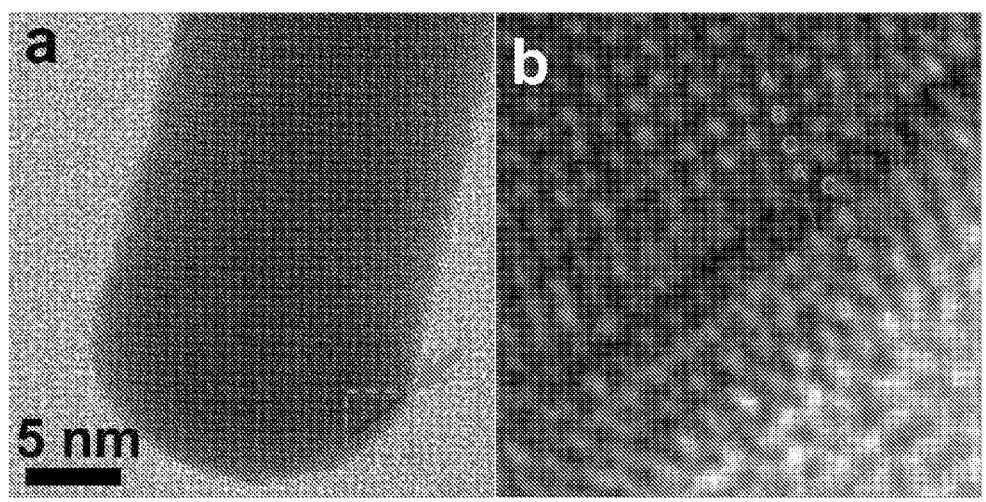
Figure 6. (a) HRTEM image of a AuNR taken at the earliest stage of the seeded growth along the [1$\bar{1}$0] axis, in which the formation of the first stacking fault at one bridging facet is captured, as indicated by the arrow. (b) Enlarged image of the highlighted region in (a) with the stacking manner of (111) planes specified.

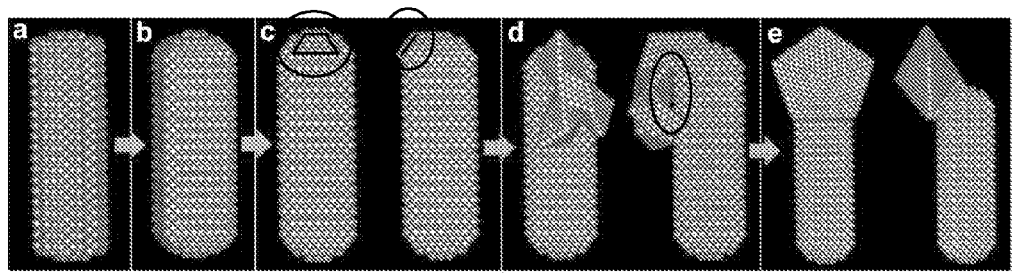

Figure 7. Schematic illustration of the growth pathway of AuNR-AuNP dimer. (a) AuNR seeds enclosed by eight symmetry-equivalent high-index {5 12 0} side facets; (b) AuNR with a tetragonal prism body mainly enclosed by {110} side and {111} bridging facets by secondary growth; Two orthogonal views of (c) initial nucleation of a stacking fault (in silver color) on one (111) bridging facet; (d) subsequent growth of Au agglomerate of small grains by random twinning; and (e) final formation of a multi-twinned particle at the neck of the AuNR after a recrystallization process. The ellipse in (d) indicates the "gap" formed between the growing Au agglomerate and the AuNR as a consequence of random twinning.

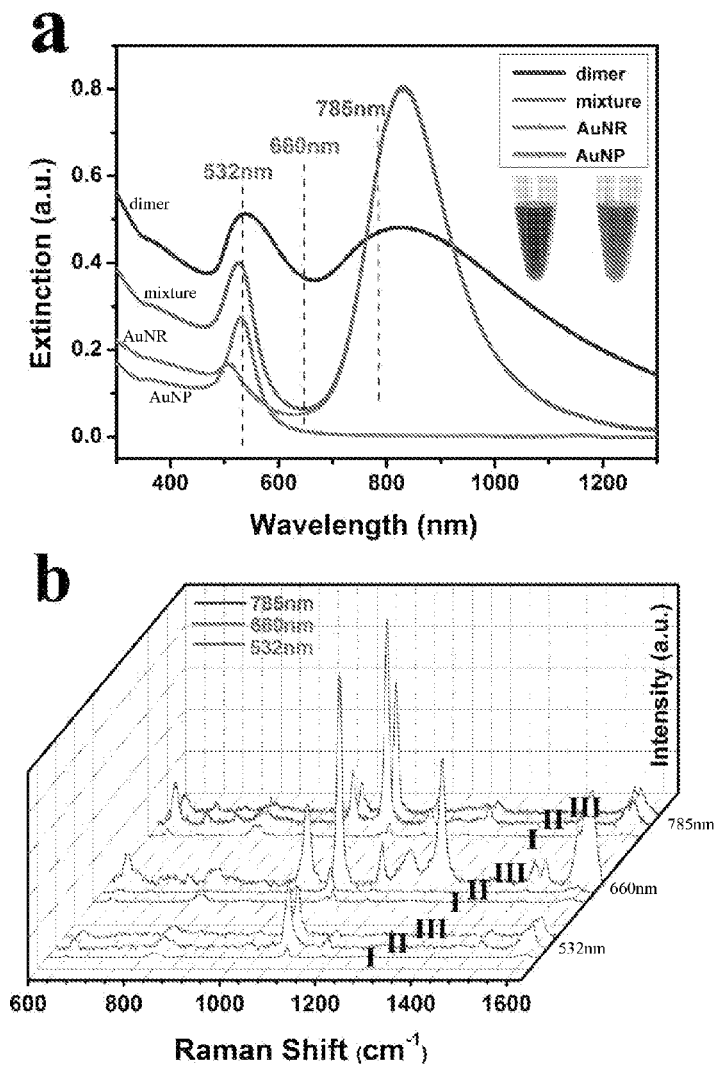

Figure 8. (a) UV-vis-NIR extinction spectra of AuNP, AuNR, AuNR/AuNP mixture, and AuNR–AuNP dimer. Insets are the photographs of the suspensions of the AuNR/AuNP mixture (wine-red in color) and the AuNR–AuNP dimer (dark-purple in color). (b) Solution Raman/colloidal SERS spectra of 4-MP probe at three different excitation wavelengths (green line: 532 nm; red line: 660 nm; purple line: 785 nm) for bulk 4-MP solution (Trace 1), AuNR/AuNP mixture (Trace II) and AuNR–AuNP dimer (Trace III).

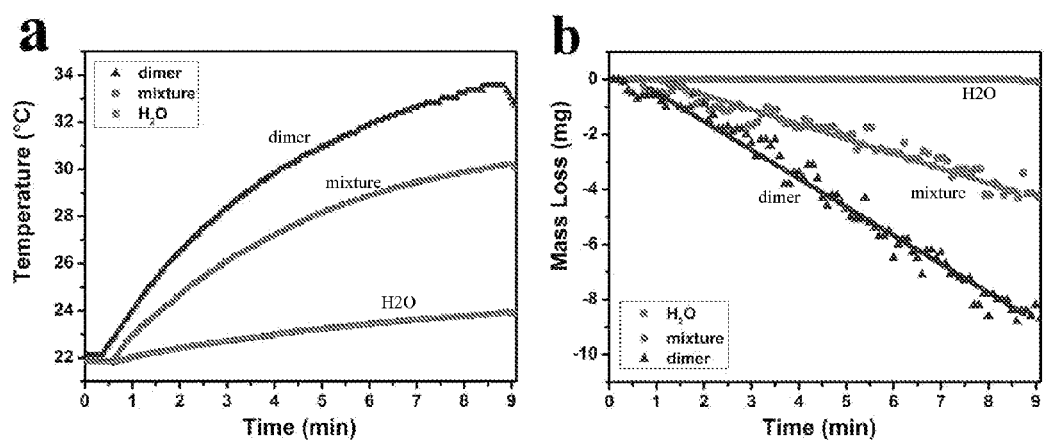
Figure 9. Measurements of (a) temperature increase due to heating of the fluid volume and (b) mass loss due to the vapor release during solar irradiation for pure $H_2O$ (green square), AuNR/AuNP mixture (wine-red dot) and AuNR–AuNP dimer (dark-purple triangle) suspensions.

ASYMMETRIC MONOMETALLIC NANOROD NANOPARTICLE DIMER AND RELATED COMPOSITIONS AND METHODS

CROSS REFERENCE TO RELATED APPLICATION

This is a national stage of PCT/IB2015/002077, filed internationally on Sep. 25, 2015, which claims priority to U.S. Provisional Application Ser. No. 62/055,369, filed on Sep. 25, 2014, both of which are incorporated by reference herein in their entireties.

INTRODUCTION

Colloidal noble metal nanocrystals (NCs) usually exhibit highly symmetric particle morphologies, as dictated by their intrinsic crystallographic symmetries. Breaking such morphological symmetry would bring vast variations in their plasmonic and chemical properties, greatly enriching their applications in plasmonics,[1] nanophotonics,[2] sensing[3] and surface enhanced Raman scattering (SERS).[4]

One effective approach to symmetry breaking is to synthesize "dimer" crystals via seeded growth, where one can vary many factors, such as the size and shape of the seeds, the type of the growth material, the choice of capping ligand, and the reaction kinetics, to manipulate the dimeric nanostructures.[5] For example, some bimetallic (e.g. Au—Ag, Pd—Ag, Pt—Ag and Pd—Au) dimers, which were also referred to as hybrid dimers or heterodimers, have been fabricated in this way.[6] However, the synthesis of monometallic dimers via seed-mediated growth is rather difficult, because one of the main driving forces for dimerization is the lattice mismatch between two materials. When the growth material is the same as the seed, epitaxial growth at the entire surface of the seed particle is favorable over the formation of a dimer.[7] On the other hand, most reported dimers are constituted by two particles,[8] whereas dimers with other configurations, for instance, a nanoparticle (NP) grown on a single-crystalline nanorod (NR) with a regular morphology, are yet to be explored. Given the high degree of symmetry of metallic structures, it is conceivable that growing a single NP on a highly regular NR is difficult because it requires one site on the NR at which the NP is grown to be differentiated from many other symmetry equivalent sites.

It is interesting to note that in addition to being a fundamental challenge in wet-chemistry, fabricating such an asymmetric monometallic dimer structure has significant implications in nanophotonics. Theoretical calculation based on Conformal Mapping Transformation[8] indicates that a dimeric NC consisting of a spherical AuNP grown on a AuNR might behave as a "black" material, with high absorption in an extremely broad spectral window ranging from near ultraviolet (UV) to far infrared (IR). This is in significant contrast to conventional plasmonic NCs, which inherently show narrow-band plasmon resonances absorption. This unique property endows the proposed AuNR-AuNP dimer with a great promise as a black super absorber to enhance the performance of photovoltaic cells, blackbody emitters, and plasmonic lasers. It would also be useful as a multiple-frequency applicable platform for photothermal conversion and field enhancement spectroscopy.

A need exists to discover improved forms of nanostructures with unexpected properties which are useful for a variety of commercial applications.

SUMMARY

Embodiments described herein include, for example, compositions, nanostructures, methods of making and methods of using such compositions and nanostructures, as well as devices and other articles comprising the compositions and nanostructures.

For example, one embodiment provides for a method comprising: reacting metallic nanorods in the presence of at least one solvent, at least one metal precursor, at least one organic ligand, and at least one reducing agent in selected amounts and reaction conditions; wherein the selected amounts and reaction conditions result in an asymmetric monometallic nanorod-nanoparticle dimer reaction product. (Herein, nanorod is NR; nanoparticle is NP; and nanocrystal is NC). One skilled in the art can vary the amounts and reaction conditions for a particular system to achieve the claimed results and advantages described herein. Another, more particular, embodiment is a method comprising: reacting gold nanorods in the presence of at least one solvent, at least one gold metal precursor, at least one organic ligand, and at least one reducing agent in selected amounts and reaction conditions, wherein the selected amounts and reaction conditions result in an asymmetric monometallic gold nanorod-nanoparticle dimer reaction product. Other components such as, for example, a surfactant can be used in some embodiments. The nanorods also can be reacted with mixtures which consist essentially of these components.

In one embodiment for these methods, the metallic nanorods are gold nanorods, the solvent is water, the metal precursor is a gold metal precursor, and the organic ligand is a thiol ligand. In one embodiment for these methods, the organic ligand is 4-mercaptophenol. In more embodiments for these methods, the concentration of the thiol ligand is at least 5 mM, or at least 10 mM. In one embodiment, the nanoparticle of the dimer reaction product has a lateral dimension size of about 10 nm to about 50 nm. In one embodiment, the nanorod and the nanoparticle of the dimer reaction product are intergrown through metallic bonding. In one embodiment, the nanorod is a single crystal nanorod. Another embodiment is a composition prepared by the methods described herein, including nanostructures and colloidal or dispersed forms of the nanostructures in a carrier.

In another embodiment, the method is for reacting metallic nanorods in the presence of at least one solvent, at least one metal precursor, at least one organic ligand, and at least one reducing agent. In one embodiment, the nanorods are gold nanorods, and the precursor is a gold precursor. For example, in one embodiment, the metallic nanorods are gold nanorods, the solvent is water, the metal precursor is a gold metal precursor, and the organic ligand is a thiol ligand. In one embodiment for this method, the organic ligand is 4-mercaptophenol. In one embodiment for this method, the concentration of the thiol ligand is at least 5 mM, or at least 10 mM. In one embodiment, the nanoparticle of the dimer reaction product has a lateral dimension size of about 10 nm to about 50 nm.

Another embodiment provides for an asymmetric monometallic nanorod-nanoparticle dimer. In one embodiment, the nanorod is a gold nanorod and the nanoparticle is a gold nanoparticle, providing for an asymmetric monometallic gold nanorod-nanoparticle dimer.

In one embodiment, the nanorod and the nanoparticle of the dimer reaction product are intergrown through metallic bonding. In one embodiment, the dimer is characterized by a strong absorption from about 300 nm to about 1,200 nm of at least 0.2 absorption units (a.u.). In another embodiment, the dimer is characterized by a strong absorption in the range from about 300 nm to about 1,200 nm of at least 0.2 absorption units (a.u.) and also has at least two peaks of at least 0.4 a.u. In another embodiment, a colloidal dispersion of the dimer is dark purple.

Further embodiments include a device comprising a composition such as the dimer described herein. In one embodiment, for example, the device is a photovoltaic device, an amplifier for a random laser, a surface enhanced spectroscopic device, or a photothermo conversion device. Other devices are described herein.

A preferred embodiment is asymmetric AuNR-AuNP dimer NCs. The inventor(s) synthesize such asymmetric AuNR-AuNP dimer NCs by using pre-synthesized AuNRs as the seeds. Previous studies demonstrated that the surface capping ligands can play a role, sometimes a crucial role, in directing the growth model in seed-mediated synthesis. For example, the use of thiol-based ligands that strongly interact with the Au seeds could induce asymmetric growth of Ag, which would otherwise form a concentric shell over the seeds due to the little lattice mismatch between Ag and Au.[6a] However, the mechanism of such ligand-induced asymmetric growth remains subject of review due to the lack of direct experimental evidence, and to the best of inventor(s)' knowledge this strategy has not been applied to grow dimers from single crystalline NCs with regular shapes.

Herein, it is described in a preferred embodiment that with properly chosen experimental variables such as ligand selection, reducing agent, and reaction conditions, asymmetric AuNR-AuNP dimers can be synthesized from single crystalline AuNR seeds. These dimers show extraordinary broadband optical extinction behavior spanning from UV to near IR, a distinguishing feature from AuNRs, AuNPs or their mixture. Using electron microscopy and tomography techniques, the inventor(s) reconstructed the three-dimensional morphology of the dimer crystal, and identified that the newly grown AuNP is a multiple twinned crystal preferentially residing at the "neck" region of the AuNR. The well-defined morphology of single crystalline AuNR (with surface facets' indices known) allows one to easily identify the formation of dimer interface and to track the subsequent evolution of AuNP. While the claimed inventions are not limited by theory, the results provide important insights into the growth mechanism of this unprecedented dimeric nanostructure, suggesting that the NP first nucleates at one (111) bridging facet of the NR, which further grows as a consequence of random twinning, and finally re-crystallizes into a single multi-twinned crystal.

The key factors for this successful synthesis of a preferred embodiment include inhomogeneous surface strains on the AuNR and appropriate reduction kinetics, which are both associated with the use of a thiol ligand, for example, 4-mercaptophenol. This mechanism explains a previously observed puzzling phenomenon that organic molecules can be embedded in "gaps" within an integrated metallic nanostructure.[6a, 9] In addition to the synthetic mechanism study, the inventor(s) successfully demonstrated the advantages of the broadband AuNR-AuNP dimer over conventional plasmonic NCs (the mixture of AuNR and AuNP) in surface-enhanced Raman scattering and solar-light harvesting.

In a preferred embodiment, asymmetric monometallic Au dimer nanocrystals have been synthesized by site-specific growth of single AuNPs on single-crystalline AuNRs. The growth pathway has been explicitly identified by detailed TEM study. Thiol-based ligand such as, for example, components such as 4-MP can play important roles in directing the formation of the dimer structure. Thermodynamically, it induces significant and inhomogeneous surface strain on the AuNR to initialize the growth of AuNP from stacking faults; kinetically, it modulates the reduction rate of the Au precursor to prevent uncontrolled deposition. The obtained AuNR-AuNP dimer exhibits a unique broadband optical extinction behavior, which is substantially distinct from the SPR-based extinction by AuNP, AuNR, and their physical mixture. The inventor(s)' results demonstrate, for example, that the broadband extinction property makes the dimer a generally applicable SERS substrate for various excitation wavelengths and an effective photothermal convertor using solar light.

BRIEF DESCRIPTION OF THE DRAWINGS

The following figures provide examples of various embodiments. The figures include colors such as red, green, silver, and purple which form part of the disclosure.

FIG. 1. TEM images of (a) the AuNR seeds and (b-d) various Au nanostructures after seeded growth with different concentrations of 4-MP: (b) peanut-shaped AuNRs (4-MP: 0 mM), (c) irregular rugged AuNRs (4-MP: 1 mM), and (d) AuNR-AuNP dimers (4-MP: 10 mM). FIG. 1(d) illustrates a preferred embodiment.

FIG. 2. (a) TEM image and (b) indexed SAED pattern of a single-crystalline peanut-shaped AuNR taken along the [1$\bar{1}$0] axis; (c) HRTEM image of the highlighted region in (a). (d) TEM image of an irregular rugged AuNR, which contains both epitaxially grown (single-crystalline) and multiple twinned domains, as indicated by the HRTEM images (e and f) and the corresponding FFT diffractograms (insets) taken from the two highlighted regions in (d).

FIG. 3. (a) TEM image a AuNR-AuNP dimer taken along the [1$\bar{1}$0] direction of the AuNR. (b) SAED pattern taken from the marked region in (a), illustrating the single-crystalline nature of AuNR in the dimer. (c) HRTEM image of the AuNR-AuNP dimer, showing single-crystalline AuNR, multiple twinned AuNP, and a stacking fault-rich interface. (d, e) FFT diffractograms of (d) region I and (e) region II marked in (c). (f) Reconstructed tomographic images of a AuNR-AuNP dimer crystal projected along four <110> directions of the AuNR. (g) A tomographic cross-section slice of the AuNR in the dimer along the [001] axis, as illustrated in (f).

FIG. 4. TEM images of various intermediates of the AuNR-AuNP dimer at different seeded growth stages, which were obtained by quenching the reaction at (a) 3, (b) 10, (c) 20, (d) 60, and (e) 180 s. The circles in (a) indicate the tiny budding particles. The arrows in (b and c) indicate worm-like agglomerates (upper red arrows) and cauliflower-like agglomerates (lower green arrows). (f) HRTEM image of the intermediate at 3 s taken along the [1$\bar{1}$0] axis of the AuNR, showing a small particle protruding from the AuNR along the [111] direction. (g, h) FFT diffractograms of (g) region I and (h) region II marked in (f). The diffuse reflections in (h) are indicative of the presence of stacking faults. (i) HRTEM image of the intermediate at 20 s taken along the [1$\bar{1}$ ] axis of the AuNR. The ellipse indicates a gap formed by the cauliflower-like agglomerate and the AuNR. (j) Enlarged HRTEM image of the interface region marked in (i), in which two arrows indicate nanotwin boundaries.

FIG. 5. (a, c) Atomic-resolution HRTEM images of (a) the as-synthesized (CTAB capped) AuNR and (c) 4-MP incubated AuNR taken along the [1$\bar{1}$0] axes. (b, d) corresponding strain distributions of the shear component ($\varepsilon_{xy}$, the magnitude cut-off is ±8%) determined by geometric phase analysis. (e, f) Enlarged Bragg-filtered HRTEM images of (f) region I and (e) region II, as marked in (c). The maxima of atomic columns are connected to form an array of rhombuses, where the resulting obtuse angles (θ) correlate with the magnitudes of the strains.

FIG. 6. (a) HRTEM image of a AuNR taken at the earliest stage of the seeded growth along the [1$\bar{1}$0] axis, in which the formation of the first stacking fault at one bridging facet is captured, as indicated by the arrow. (b) Enlarged image of the highlighted region in (a) with the stacking manner of (111) planes specified.

FIG. 7. Schematic illustration of the growth pathway of AuNR-AuNP dimer. (a) AuNR seeds enclosed by eight symmetry-equivalent high-index {5 12 0} side facets; (b) AuNR with a tetragonal prism body mainly enclosed by {110} side and {111} bridging facets by secondary growth; Two orthogonal views of (c) initial nucleation of a stacking fault (in silver color at top, each encircled) on one (111) bridging facet; (d) subsequent growth of Au agglomerate of small grains by random twinning; and (e) final formation of a multi-twinned particle at the neck of the AuNR after a recrystallization process. The ellipse in (d) indicates the "gap" formed between the growing Au agglomerate and the AuNR as a consequence of random twinning.

FIG. 8. (a) UV-vis-NIR extinction spectra of AuNP, AuNR, AuNR/AuNP mixture, and AuNR-AuNP dimer. Insets are the photographs of the suspensions of the AuNR/AuNP mixture (wine-red in color at right) and the AuNR-AuNP dimer (dark-purple in color at left). (b) Solution Raman/colloidal SERS spectra of 4-MP probe at three different excitation wavelengths (green lines (lower): 532 nm; red lines (middle): 660 nm; purple lines (upper): 785 nm) for bulk 4-MP solution (Trace 1), AuNR/AuNP mixture (Trace II) and AuNR-AuNP dimer (Trace III).

FIG. 9. Measurements of (a) temperature increase due to heating of the fluid volume and (b) mass loss due to the vapor release during solar irradiation for pure H$_2$O (green square), AuNR/AuNP mixture (wine-red dot) and AuNR-AuNP dimer (dark-purple triangle) suspensions.

DETAILED DESCRIPTION AND WORKING EXAMPLES

Priority U.S. provisional application Ser. No. 62/055,369 filed Sep. 25, 2015 is hereby incorporated by reference in its entirety including figures and working examples. References cited herein are incorporated by reference. No admission is made that any of these references are prior art.

Additional embodiments are provided in the following detailed description, non-limiting working examples, and descriptions thereof. The claimed inventions are broader than the representative, non-limiting working examples. For example, other metals, metallic nanorods, solvents, metal precursors, organic ligands, reducing agents, and reaction conditions can be used. The particular reaction conditions for a successful synthesis may need to be adjusted for a particular use of combinations of structures such as the metal, the nanorod, the solvent, the precursor, the organic ligand, and the reducing agent. Solvents, solvent systems, and solvent mixtures are known in the art including use of water and, more particularly, use of water as a primary solvent so as to provide an aqueous solution. The amount of water in the aqueous solution can be, for example, at least 70 wt. %, or at least 80 wt. %, or at least 90 wt. %, or at least 95 wt. % with respect to a mixture of solvents. Organic solvent can be excluded. The amount of water in the solvent system can be essentially 100 wt. %. Also, organic ligands for metals and gold metal are known in the art. In addition, reducing agents are known in the art. One or more surfactants can also be used as known in the art. The particular reaction conditions with selection of ingredients and amounts also can be adapted as the reactions are scaled up for commercial applications.

In a preferred embodiment, single-crystalline AuNRs [length=(75.3±7.4) nm, width=(18.4±1.7) nm] were synthesized using the well-established seed-mediated method (FIG. 1a).[10] Several recent studies consistently revealed that these AuNRs are grown along the [001] direction, and enclosed by eight symmetry-equivalent high-index {5 12 0} side facets.[11] To grow AuNR-AuNP dimers, the as-synthesized AuNRs were first incubated with thiol ligand 4-mercaptophenol (4-MP), followed by the addition of new Au precursor (e.g., HAuCl4) and reducing agent (e.g., ascorbic acid). It was found that the concentration of 4-MP in the solution determines the final Au nanostructure.

At the absence of 4-MP in the system, a layer of Au was continuously grown around the AuNR with a preference for the rod ends, leading to a "peanut" shape of the final structure (FIG. 1b). Selected-area electron diffraction (SAED) demonstrated that each "peanut" remains a single crystal, while high-resolution TEM (HRTEM) image accordingly showed clear epitaxial interface between the newly grown layer and the original NR (FIGS. 2a-c). When the AuNRs were incubated with 1 mM of 4-MP, the growth of Au on the seed crystals was irregular, resulting in NRs with rugged surfaces (FIG. 1c). Careful TEM investigation revealed that the newly grown Au layer was mainly composed of multiple-twinned crystals (FIGS. 2d, f), while epitaxial growth was also observed at the rod ends (FIGS. 2d, e). These observations suggest that two different mechanisms of secondary growth coexist at this condition. Interestingly, when the concentration of 4-MP was increased to 10 mM, the designated AuNR-AuNP dimer structure was successfully produced with a high yield (>90%), in which a single AuNP (about 30 nm) is located at the "neck" region (with a few exceptions) on each individual AuNR that is otherwise nearly unchanged (FIG. 1d). As illustrated by SAED and HRTEM, the AuNR in the dimer remains single crystalline with smooth surfaces (FIGS. 3a-d), whereas the AuNP is a multiple-twinned crystal (FIG. 3c). Successive nanotwins at the interface between the NP and NR were observed in the HRTEM image (FIG. 3c) and confirmed by the diffuse streaks along the [111] direction in the FFT (FIG. 3e). The fact that the AuNR and AuNP are intergrown through metallic lattice (metallic bonding) distinguishes the AuNR-AuNP dimer from those previous dimer structures formed by the assembly of two separate particles with the help of surface ligands.[2-4a, 12]

These results indicate that with high concentration of 4-MP, the continuous epitaxial growth of Au layer was essentially inhibited, whereas the asymmetric growth of twinned particle became dominant. In this sense, the irregular rugged AuNRs synthesized with a medium concentration of 4-MP (i.e. 1 mM) can be considered as an intermediate between the "peanut" and the "dimer".

To the best of the inventor(s)' knowledge, a colloidal plasmonic metal structure integrating an anisotropic nanorod with a nanoparticle in the form of a dimer has not been fabricated before. The inventor(s) resorted to electron tomography to reconstruct individual dimer crystals from a series of HAADF-STEM images, which allows for better understanding of this structure through 3-D visualization. The result illustrates that the multiple-twinned AuNP has a flattened ellipsoid shape and it is connected with the AuNR at one rod end, giving rise to an overall sunflower-like morphology of the dimer. FIG. 3f shows typical reconstructed tomographic images of a dimer projected along four <110> directions of the AuNR (i.e., 90 degree rotation with each other along the rod axis). Moreover, tomography reveals that unlike the original AuNR seed, which can be described as an octagonal prism with a rather round cross section,[10a,11] the AuNR in the dimer is more approximate to a truncated tetragonal prism with four {110} facets as the main side surfaces (FIG. 3g). This suggests that during the formation of the NP at the rod end, slight evolution of the rod body also occurred as a consequence of slow deposition of Au, converting high-indexed side surfaces to low-indexed ones.

The inventor(s) have reconstructed more than one AuNR-AuNP dimer crystals using HAADF-STEM tomography, and found that the NPs formed on different NRs are of similar position and orientation relative to the NR, whereas their exact sizes and shapes are not completely identical. A common feature of these AuNPs is that they are multiple-twinned crystals connecting with the single-crystalline NRs through twin boundaries as the interface.

When the concentration of 4-MP in the system was further increased (greater than 15 mM), no obvious secondary growth on the AuNR seeds was observed after the same reaction time, possibly because the reduction of Au ions was inhibited by highly concentrated 4-MP ligands. It was also found that the reaction for the peanut-shaped AuNRs was completed (no obvious further change in size and morphology) within about 5 s after the initialization of the reduction, while the time required for the formation of AuNR-AuNP dimers was >60 s (vide infra).

These observations suggest a correlation between the reduction rate of Au precursor and the final nanostructure, where the dimer structure is favored by relatively slow reaction kinetics. To verify this, the inventor(s) modified the afore-described synthetic system for the dimer structure (4-MP: 10 mM) to increase the reduction rate by either elevating the concentration of ascorbic acid (from 7.5 to 15 mM), or replacing ascorbic acid with sodium ascorbate, or heating the reaction solution (from RT to 45° C.). In all cases, irregular NRs instead of dimers were produced after Au reduction. These results illustrate the important influence of reduction rate on the formation of dimer structure.

There are two possible reasons for the slow reduction rate associated with high concentration of 4-MP. First, thiol-ligands and $AuCl4^-$ ions form more stable thiolate-Au(I) complexes with lower reduction potentials;[13] Second, thiol-ligands occupy the surface sites of AuNRs by strong chemical adsorption, inhibiting the reduction of Au(I) ions by ascorbic acid for which the exposed Au surface acts as a catalyst.[14]

However, controlled reduction kinetics of Au ions is a necessary but insufficient condition for the formation of the AuNR-AuNP dimer structure, because when the concentration of 4-MP was low, dimers could not be obtained no matter how the reduction rate was reduced by varying other conditions, e.g., by using lower temperatures or less amount of ascorbic acid. In another control experiment, equal amounts of as-synthesized AuNRs (without incubation with 4-MP) and 4-MP incubated AuNRs were mixed and then used as seeds for the synthesis of dimer structure, keeping the other conditions identical. As being in the same reaction system, the two types of AuNRs were supposed to experience the same reaction kinetics. However, we found that the product was a roughly 1:1 mixture of peanut-shaped crystals and dimer crystals. Therefore, in addition to the reaction rate control, the ligand 4-MP must have other role(s), most likely from the thermodynamic aspect, in directing the formation of the dimer structure. Understanding the roles of 4-MP would be helpful to answer some yet unsolved questions relevant to the dimer structure: (i) why are AuNPs site-specifically grown at the "neck" region of the AuNR? (ii) why are AuNPs all multiple-twinned crystals? (iii) why is there only one AuNP grown at one out of many symmetry equivalent sites for each AuNR? (iv) how does the concentration of 4-MP influence the mechanism of secondary growth?

The relatively slow reaction kinetics for the growth of the dimer structure allows one to track the evolution of the AuNP on the AuNR by quenching the reaction to get intermediates and investigating them with TEM. FIG. 4 shows TEM images of the products at different reaction time after the addition of ascorbic acid: 3, 10, 20, 60, and 180 s. In the sample of 3 s, the initial emergence of AuNP on the AuNR was observed. As shown in FIG. 4a, most AuNRs have a small Au particle (~3 nm) protruding from the "neck" region. HRTEM image clearly shows that the small particle is grown from the NR along the [111] direction (FIG. 4f). Different from the defect-free body of the AuNR, the budding AuNP contains stacking faults, as illustrated by the FFTs (FIGS. 4g, h). In the next stage of the reaction (3 s to 20 s), the tiny Au buds gradually grew into larger irregular agglomerates of small grains with two typical overall morphologies: cauliflower-like and worm-like (FIGS. 4b, c). HRTEM images indicate that regardless of the morphology, these agglomerates are full of randomly grown nanotwins (large stacking faults) (FIG. 4i). As in the case of the final dimer structure, twin boundaries were clearly observed at the interface between the AuNR and the growing agglomerate (FIGS. 4i, j). Interestingly, the obvious difference in morphology evanished as the reaction time was prolonged. In the sample of 60 s, most AuNRs have a nearly round AuNP (FIG. 4d), which resemble the NPs in the final dimers (i.e., the 180 s sample, FIG. 4e) but have rougher surfaces and smaller sizes.

It is known that strong ligands could induce remarkable strains on a metal surface,[15] which in turn modulate its stacking-fault energy (SFE).[16] Such strains are usually inhomogeneous over the entire crystal surface, with their types and magnitudes depending on the exposed facets and the local surface curvature. Different surface strains influence the SFE differently. When certain strain lowers the SFE, the formation of stacking faults or nanotwins in the crystal is promoted.[16a] In the present synthetic system, anisotropic AuNR was incubated with 4-MP (a strong thiol-based ligand) before growing the dimer structure. The 4-MP ligand would give rise to non-uniform surface strain field on the AuNR, which helps to differentiate different crystal facets and "magnify" the tiny structural difference between symmetry-related sites (the strain is highly sensitive to local surface curvature). This might account for the observed site-specific growth of one AuNP on the AuNR in the dimer. Meanwhile, the 4-MP induced surface strain reduces the SFE, facilitating the growth of AuNP in the form of successive nanotwins.

On the basis of these observations and analysis, it is proposed that a growth mechanism of the AuNP in the dimer structure as follows, recognizing that the claimed invention is not limited by theory. The chemisorption of 4-MP ligands induces inhomogeneous strains on the surface of AuNR. Among different surface facets of the AuNR, the (111) bridging facets at the rod "neck" are the most strained and thus preferential for Au deposition to form a twinning structure via stacking faults that can largely relieve the surface strain.[17] Once the first twin structure is formed on a (111) facet, this facet is differentiated from other symmetry equivalent facets, becoming an "active" site for the further growth of Au through successive twinning, as driven by the same strain-relief mechanism (FIG. 4a). New twins can be formed randomly in different <111> directions, resulting in various agglomerates of small grains. Worm-like structures are formed when most new grains grow laterally along the rod, while a radiative twinning manner leads to cauliflower-like structures (FIGS. 4b, c). At the final stage of the synthesis, the agglomerates undergo a recrystallization process with small grains fused into large ones, accompanied by the disappearance of grain boundaries. As a consequence, different-looking agglomerates gradually develop into single AuNPs of similar shapes, and with prolonged reaction these NPs have less grains and smoother surfaces (FIGS. 4d, e).

The key hypothesis of this proposed mechanism is that 4-MP ligand can induce significant and inhomogeneous surface strain on the AuNR. In order to verify this hypothesis, the inventor(s) characterized using HRTEM the as-synthesized AuNR (with weaker ligand CTAB) and 4-MP incubated AuNR, and visualized their strain distributions with geometric phase analysis (GPA).[18] Atomic-resolution HRTEM images were taken for both types of AuNR along the axes, as the displacement of the densely packed (111) layers can be identified in this direction (FIGS. 5a, c). Interestingly, the GPA analysis shows that unlike the as-synthesized AuNR that has little strain fluctuation over the entire crystal (FIG. 5b), the 4-MP incubated AuNR exhibits large shear deformation on the rod surface, which is particularly localized on the (111) bridging facets at the "neck" regions (FIG. 5d). Aligning the y-axis of GPA map with the growth direction (i.e. the [001] axis) of the AuNR, the shear strain fields ($\varepsilon_{xy}$) in left and right bridging facets have opposite signs, indicating the same type of shear deformation caused by the glide of {111} planes (FIG. 5d). The shear strain was determined to be the <11$\bar{2}$>{111} slip following the alias regime.[16b] In the Bragg-filtered HRTEM image of the 4-MP incubated AuNR, an array of rhombuses are delineated by connecting neighboring atomic columns (FIGS. 5e, f). The magnitudes of the strains at different areas can be intuitively identified from the obtuse angles (θ) of the rhombus. Specifically, the angles measured at the side surface of rod body (θ: 108.1°-109.9°) are very close to the value for a perfectly ABC stacked bulk structure (θ=109.6°) (FIG. 5f), whereas much smaller angles (θ: 102.5°-104.3°) are observed at the bridging facets (FIG. 5e). These results clearly demonstrate that 4-MP can selectively induce large surface strain at the "neck" region of the AuNR, where the surface (111) planes undergo shear deformation along the [11$\bar{2}$] direction.

Theoretically, unstable stacking fault (USF) at a displacement of half Burgers vector (0.5|$\vec{bp}$|, 1/12 [11$\bar{2}$]) represents a barrier for the nucleation of stable intrinsic stacking fault (ISF) at $\vec{bp}$=1/6 [11$\bar{2}$] Shear deformation overcoming this barrier would cause the spontaneous formation of stacking faults. In fact, it is known that the shear deformation along the [11$\bar{2}$] direction can lead to a sharp decrease of the SFE before reaching that critical magnitude (0.5|$\vec{bp}$|). 16b In our synthesis system, we found that although almost all the observed bridging (111) facets in the 4-MP incubated AuNR have obvious shear strains, the absolute magnitudes of the strains vary from case to case. For instance, in the AuNR shown in FIG. 5d, the right bridging facet has markedly greater shear strain than does the left counterpart (10% vs. 5%). This means that the intrinsic symmetry of the AuNR can be broken upon the exertion of uneven ligand-induced surface strains. Consequently, symmetry-equivalent surface facets are discriminated from each other by their different SFEs, and the nucleation of stacking faults would preferentially take place at the one with the lowest SFE. This explains the fact that AuNP grows from only one of eight symmetry-related {111} bridging facets on the AuNR.

It was useful to capture the occurrence of the first stacking fault from a AuNR. Different from most AuNRs in the sample of 3 s, this particular NR is at an even earlier stage (likely the earliest stage) of the seeded growth, in which the first stacking fault is clearly observed at the right bridging facet (FIGS. 6A, B). This observation strongly supports our hypothesis that the nucleation of the AuNP starts from a stacking fault formed on the most strained bridging facet. The appearance of the stacking fault and the subsequent twinning structures at only one bridging facet further breaks the symmetry of AuNR. The misstacking of atoms produces reentrant edges, accelerating the crystal growth along the boundary.[19] Meanwhile, the vicinity of a twin boundary has lower SFEs, where the nucleation of new stacking faults is greatly facilitated.[20] In this sense, the growth of AuNP from the first stacking fault through continuous twinning is a self-accelerating and highly favorable process, which largely inhibits the nucleation/growth of new AuNPs on other sites of the AuNR.

With the gradual decrease of HAuCl$_4$ concentration in the system, a slower "recrystallization" process becomes dominant. This is because irregular agglomerates of small grains are thermodynamically unstable, which tend to ripen into larger crystals with less grain boundaries and smaller surface-to-volume (S/V) ratios to decrease the surface energy. Eventually, single large AuNPs (about 30 nm) are evolved at the "neck" regions of the AuNRs, which have multiply-twinned structures close to decahedra or icosahedra. During the TEM characterization of the sample of 20 s, one indeed observed the evolution of irregular agglomerates into a single particle that was induced by prolonged electron beam irradiation. Based on this observation and the well-recognized high mobility of metal atoms in nano-sized crystals,[21] it is plausible to speculate that the recrystallization takes place through the migration of Au atoms in solid phase, without dissolution and re-deposition processes. We note that a small fraction of dimers have the AuNPs located at the body (instead of the neck) of the AuNRs (FIG. 1d). This is probably due to the migration of Au atoms during the recrystallization that occasionally deviates the final AuNP migrating from the original nucleation sites.

A schematic illustration of the growth pathway of the AuNR-AuNP dimer structure is shown in FIGS. 7A-E. It was recently proposed that thiol-based molecules can be embedded in metallic nanostructures during their growth, forming a "gap" in the final integrated crystals.[6a, 9] Although being supported with experimental observations, the embedment of organic molecules within the lattice of metallic crystals seems very unusual and contradictory to the conventional wisdom. Interestingly, we can easily observe such intracrystal "gaps" in our synthetic system, especially in the intermediate states (FIG. 4i), and their formation can be well explained with our afore-described mechanism as a consequence of random twinning. That is, a gap is formed when a part of a growing Au agglomerate happens to contact and thus interconnect with the NR after continuously and randomly twinning (FIGS. 4i, 7d). As such, it is possible that surface ligand molecules are embedded in an overall integrated Au crystal.

The proposed mechanism (that is, ligand-induced inhomogeneous surface strains account for the asymmetric growth of AuNP on the AuNR) is mainly based on discussions from a thermodynamic perspective. The question about the influence of the concentration of 4-MP, which determines not only the surface strains on Au NR seeds but also the reduction rate of the Au precursor, on the secondary growth of Au has yet to be fully addressed (FIG. 1). To achieve a thermodynamically controlled process requires sufficiently slow reaction kinetics. As discussed earlier, a higher 4-MP concentration leads to a slower reduction rate in this system. In the absence of 4-MP, the AuNR has trivial surface strain and epitaxial growth is therefore highly favored even with a fast reduction rate (FIG. 1b). On the other extreme, an optimally high concentration of 4-MP induces strong inhomogeneous strains on the AuNR surfaces to distinguish one bridging facet for nucleation, and at the same time results in a slow reduction rate to ensure thermodynamically controlled growth of AuNP at the sole nucleation site (FIG. 1d). With a medium concentration of 4-MP, despite the existence of local surface strains, the relatively fast reduction rate leads to indiscriminate crystal growth on the AuNR in both twinning and epitaxial manners. Consequently, irregular NRs with different secondary growth mechanisms are obtained (FIG. 1c).

Optical Properties

To verify the optical properties of this novel AuNR-AuNP dimer, its UV-Vis-NIR extinction spectrum was collected and compared with that of AuNP, AuNR, and their physical mixture (denoted as AuNR/AuNP mixture) (FIG. 8a). The AuNPs used for comparison were similar in size to the AuNPs in the dimer (about 30 nm). Their suspension showed the characteristic Surface Plasmon Resonance (SPR) band at 528 nm. The AuNRs used for comparison were the seeds for the synthesis of dimer, which exhibited the transverse SPR at 508 nm and longitudinal SPR at 835 nm. When the AuNP suspension and AuNR suspension of nearly same particle concentrations were mixed, the resulting AuNR/AuNP mixture suspension remained two SPR bands in the spectrum at 523 and 835 nm, respectively. The spectrum of the AuNR/AuNP mixture approximated to the linear superposition of those of AuNP and AuNR alone, indicative of a negligible inter-crystal plasmonic interaction in the dilute suspension. Interestingly, the suspension of AuNR-AuNP dimer, which was controlled to have the same Au atom concentration as the AuNR/AuNP mixture suspension, exhibited a spectrum of marked difference, in which the resonance bands (about 540 and about 815 nm) are still discernable but much less remarkable relative to the extinction at other wavelengths. In comparison with the AuNR/AuNP mixture, the dimer has significantly higher extinction over the entire spectrum range (300-1300 nm) except for a small region associated with the LSP of AuNR (765-925 nm). The difference between the mixture and the dimer in extinction behavior is vividly reflected by their different colors of suspension: the former is wine-red, while the latter is dark purple (Inset of FIG. 8a). These results demonstrate that the AuNR-AuNP dimer behaves like a "black-body" with capability to absorb incident electromagnetic radiation spanning near UV, visible, and infrared regions. The physical mechanism behind such a unique broadband absorption property will be discussed elsewhere separately.

Novel applications of the AuNR-AuNP dimer include plasmonic lasing and photovoltaic devices, and it is here demonstrated the merits of its broadband extinction through two experiments: (i) surface-enhanced Raman scattering (SERS) at various excitations, and (ii) photothermal conversion under solar light. These two applications make use of the two different components of the extinct light respectively (the scattered light for SERS and the absorbed light for photothermal conversion), and they would both benefit from the broadband extinction property of the dimer.

The SERS activities of the AuNR-AuNP dimer and the AuNR/AuNP mixture were measured in dilute suspension with different excitations (i.e., 532, 660, and 785 nm), using 4-MP as the probe molecule. The concentrations of AuNP and AuNR were controlled to be approximately same in the two suspensions. The normal Raman spectra of 4-MP was collected from its bulk solution (Trace I in FIG. 8b) and used as benchmarks for the calculation of Enhancement Factor (EF). As shown in FIG. 8b, the dimer and the mixture gave comparable SERS signals for the adsorbed 4-MP at the excitations of 532 and 785 nm, which are close to the two SP resonance peaks of the mixture (EF at 532 nm: $1.3 \times 10^5$ vs. $1.7 \times 10^5$; EF at 785 nm: $3.4 \times 10^5$ vs. $5.3 \times 10^5$). In contrast, at the off-resonance condition (i.e., using excitation of 660 nm), where the dimer has much higher extinction intensity than the mixture, the dimer gave an EF as high as $5.4 \times 10^5$, about 10-fold greater than that of the mixture ($6.0 \times 10^4$). These results are well consistent with the spectra, confirming the broadband extinction property of the dimer, which enables it to act as an effective SERS substrate generally suitable for various excitation wavelengths.

The broadband extinction ability also makes the AuNR-AuNP dimer potentially useful for solar-light harvesting. It has been well established that the absorbed light energy, if not reradiated through light scattering, is dissipated through Landau damping (nonradiative) which would lead to a dramatic rise in the temperature in the nanometer-scale vicinity of the particle surface.[22] In an experiment to verify this, it was investigated the photothermal effect of the AuNR-AuNP dimer in aqueous suspension under the irradiation of solar simulator (AM 1.5G). The generated heat energy can be partitioned into two parts: one resulted in the generation of steam and the other went into the heating of the liquid.[22b] To quantify the energy efficiency, we monitored both the mass loss caused by vapor release (including steam and natural evaporation) and the temperature increase due to the liquid heating (FIGS. 9a, b). An aqueous suspension of the AuNR/AuNP mixture (having the same Au atomic concentration as the dimer suspension) and pure $H_2O$ of equal volumes were also examined for comparison. We analyzed the energy distribution between the steam release and liquid heating on the basis of the experimental data. For constant incident solar energy, the mass loss of pure $H_2O$ was trivial and the temperature increase was less than 2° C. in 7.5 min (0.5-8 min). The temperature increases over the same irradiation period for the dimer and mixture suspension were 11.1 and 8.0° C., corresponding to an energy consumption of 23.3 and 16.8 J, respectively (FIG. 9a). In the meanwhile, the dimer suspension underwent more mass loss than the mixture suspension (7.9 vs. 3.6 mg) (FIG. 9b). However, the mass losses of both suspensions were found to be mainly contributed from the natural evaporation at elevated temperatures, which suggests that the mass loss due to steam generation in this work can be neglected. This negligible steam generation is probably due to the employed low light intensity (i.e., 100 W/m$^2$).[23] Given that the solar energy available to the systems over this period was 58.5 J, the solar to thermal energy conversion efficiency are approximately 39.8% and 28.7% for the dimer and the mixture, respectively. This result represents a good example where the "black-body" absorption of the AuNR-AuNP dimer is advantageous over the narrow-band resonance absorption of conventional plasmonic NCs.

EXPERIMENTAL

Synthesis of Au Nanorods (AuNRs). The AuNRs were grown using a reported seeded growth method.[10] Specifically, the seed solution was made by injecting a freshly prepared, ice-cold aqueous NaBH$_4$ solution (0.01 M, 0.6 mL) into an aqueous mixture composed of HAuCl$_4$ (0.01 M, 0.25 mL) and CTAB (0.1 M, 9.75 mL), followed by rapid inversion for 2 min. This resulting seed solution was aged at room temperature for at least 2 h to ensure the complete decomposition of the excess NaBH$_4$. The growth solution was prepared by the sequential addition of aqueous HAuCl$_4$ (0.01 M, 2.0 mL), AgNO$_3$ (0.01 M, 0.4 mL), HCl (1.0 M, 0.8 mL), and AA (0.1 M, 0.32 mL) solutions into an aqueous CTAB (0.1 M, 40 mL) solution. After gently shaking this growth solution for 30 s, 0.15 mL of the seed solution was injected. The resulting reaction solution was gently mixed by inversion for 10 s and then left undisturbed at room temperature overnight. The obtained nanorods were washed via centrifugation two times: 1) at 7830 rpm for 30 min, followed with the removal of the supernatant solution and redispersion into 40 mL of deionized H$_2$O; 2) at 7830 rpm for 30 min, followed with the removal of the supernatant solution and redispersion into 30 mL of deionized H$_2$O.

Synthesis of Au Nanoparticles (AuNPs: About 30 nm). The growth of AuNPs was achieved using a modified reported seeded growth method.[24] The seed solution was made by injecting a freshly prepared, ice-cold aqueous NaBH$_4$ solution (0.01 M, 0.3 mL) into an aqueous mixture composed of HAuCl$_4$ (0.01 M, 0.125 mL) and CTAB (0.1 M, 3.75 mL), followed by rapid inversion for 2 min. This resulting seed solution was aged at room temperature for 1 h to ensure the complete decomposition of the excess NaBH$_4$, and then diluted by 10 times with H$_2$O. The growth solution was prepared by the sequential addition of aqueous CTAB (0.1 M, 6.4 mL), HAuCl$_4$ (0.01 M, 0.8 mL), and AA (0.1 M, 3.8 mL) into water (32 mL). After gently shaking this growth solution for 30 s, 200 uL of the diluted seed solution was injected into the growth solution. The resulting reaction solution was gently mixed by inversion for 10 s and then left undisturbed at room temperature overnight.

Synthesis of AuNR-AuNP Dimers. In a standard synthesis, 0.25 mL of as-synthesized AuNRs [length=(75.3±7.4) nm, width=(18.5±1.7) nm, concentration=about 337 pM in number of particles,] were centrifuged and then redispersed into a freshly prepared cetrimonium bromide (CTAB, 0.5 mL, 10 mM) solution and 255 uL H$_2$O. Subsequently, the ligand 4-MP (28.3 uL, 10 mM) was injected, followed by a gentle vortex of 5 s. The obtained mixture was then aged at room temperature for the purpose of incubating the AuNRs with 4-MP. After 1 h's incubation, HAuCl$_4$ (20 uL, 7.5 mM) and ascorbic acid (30 uL, 7.5 mM) were sequentially added, followed by a gentle vortex of 5 s after each addition of the chemical. The resulting mixture was then left undisturbed at room temperature for 5 min. Finally, the product was washed and collected via centrifuge at 7800 rpm for 8 min. To quench the synthesis at different time points, 100 uL of the reaction solution was quickly injected into 15 mL of ice-cold H$_2$O, and then immediately subjected to a cryo centrifuge (7830 rpm, 5 min) at −2° C.

Preparation of AuNR/AuNP Mixtures. The mixtures were prepared by mixing the same amount (particle number) of the as-synthesized AuNRs and AuNPs as that of those in AuNR-AuNP dimers. Because the AuNRs and AuNPs in the mixture have roughly the same size to those in AuNR-AuNP dimers, the overall atomic concentration of Au is also identical for the mixture and dimer. The calculation of the particle number was based on TEM images and ICP-OES. As an example, the particle number of dimers in a standard synthesis was approximately 5.06×10$^{10}$. Therefore, to prepare the AuNR/AuNP mixture, 5.06×10$^{10}$ particles of AuNRs (from the same batch as that used for the synthesis of the dimers) were mixed with 5.06×10$^{10}$ particles of AuNPs (about 30 nm in diameter).

Characterizations.

Extinction spectra were taken on a Varian Cary 5000 UV-vis-NIR spectrophotometer. SERS spectra were recorded on a Horiba Jobin Yvon LabRAM HR-800 spectrophotometer coupled to an Olympus confocal microscope (BX41) with a ×50 objective (NA=0.50) in the backscattering configuration with 532, 660 and 785 nm laser excitations. To monitor the mass loss and fluid heating, solar simulator (AM 1.5G, 100 mW/cm$^2$, Newport 91160-1000) was used to irradiate the dimer or mixture suspension (about 4.05×10$^{11}$ particles/mL) or pure H$_2$O through an optical cuvette (L×W×H: 10×4.5×13 mm) that was placed on an analytical balance (Mettler Toledo, 0.1 mg resolution). The temperature was recorded by an online-type thermocouple thermometer (DT-8891E Shenzhen Everbest Machinery Industry Co., Ltd., China with a resolution of 0.1° C.). Low-magnification transmission electron microscopy (TEM) images were acquired on a FEI-Tecnai T12 microscope operated at 120 kV. High-resolution TEM imaging and STEM tomography were carried out on a FEI-Titan ST electron microscope operated at 300 kV. An electron tomography tilt series from −74° to 74° at 1° intervals was first aligned and then reconstructed to a 3-D volume using the SIRT function in the FEI Inspect 3D software. The 3-D isosurface rendering, density segmentation and volume manipulation were then achieved by the Avizo software.

REFERENCES CITED IN APPLICATION (1) (a) Lombardi et al. *ACS Nano* 2013, 7, 2522. (b) Huang, F.; Baumberg, J. J. *Nano Lett.* 2010, 10, 1787.
(2) Bidault et al. *J. Am. Chem. Soc.* 2008, 130, 2750.
(3) Cheng et al. *Langmuir* 2011, 27, 7884.
(4) (a) Ringler et al. *Nano Lett.* 2007, 7, 2753. (b) Li et al. *Nano Lett.* 2009, 9, 485. (c) Li et al., *Angew. Chem. Int. Ed.* 2010, 49, 164. (d) McMahon et al. *Anal. Bioanal. Chem.* 2009, 394, 1819. (e) Kleinman et al., *J. Am. Chem. Soc.* 2013, 135, 301. (f) Chen et al. *J. Am. Chem. Soc.* 2010, 132, 3644.
(5) Carbone et al. *Nano Today* 2010, 5, 449.
(6) (a) Feng et al. *J. Am. Chem. Soc.* 2012, 134, 2004. (b) Lee et al. *J. Am. Chem. Soc.* 2014, 136, 5221. (c) Zhu et al. *J. Am. Chem. Soc.* 2012, 134, 15822. (d) Lee et al. *J. Am. Chem. Soc.* 2012, 134, 5456. (e) Zeng et al. *Angew. Chem. Int. Ed.* 2012, 51, 2354.
(7) (a) Zeng et al. *Nanocrystal* (Chapter 3); Publisher: InTech, 2011. (b) Sohn et al., *ACS Nano* 2009, 3, 2191. (c) Peng et al. *Nano Today* 2009, 4, 143.

(8) (a) Leonhardt, U. *Science* 2006, 312, 1777. (b) Pendry et al. *Science* 2006, 312, 1780
(9) Lim et al. *Nat. Nanotechnol.* 2011, 6, 452.
(10) (a) Huang et al. *J. Am. Chem. Soc.* 2013, 135, 8552. (b) Ni et al. *ACS Nano* 2008, 2, 677.
(11) (a) Katz-Boon et al. *J. Nano Lett.* 2011, 11, 273. (b) Carbó-Argibay et al. *Angew. Chem. Int. Ed.* 2010, 49, 9397. (c) Goris et al. *Nat. Mater.* 2012, 11, 930.
(12) (a) Zhu et al. *Small* 2012, 8, 1857. (b) Busson et al. *Nano Lett.* 2011, 11, 5060. (c) Wang et al. *Nano Lett.* 2008, 8, 2643. (d) Yim, T. J.; Wang, Y.; Zhang, X. *Nanotechnology* 2008, 19, 435605. (e) Sardar, R.; Heap, T. B.; Shumaker-Parry, J. S. *J. Am. Chem. Soc.* 2007, 129, 5356.
(13) Yuan et al. *Angew. Chem. Int. Ed.* 2014, 53, 4623.
(14) (a) Jana et al. *Chem. Mater.* 2001, 13, 2313. (b) Gole et al. *J. Chem. Mater.* 2004, 16, 3633.
(15) Watari et al. *Nat. Mater.* 2011, 10, 862.
(16) (a) Branicio et al. *Phys. Rev. B* 2013, 88, 064104. (b) Jahnátek et al. *Rev. B* 2009, 79, 224103. (c) Brandi et al. *Phys. Rev. B* 2007, 76, 054124.
(17) Paine et al. *J. Electron. Mater.* 1991, 20, 735.
(18) Hÿtch et al. *Ultramicroscopy* 1998, 74, 131.
(19) (a) Kobayashi et al. *Philos. Mag. A* 1979, 40, 399. (b) H. Hofmeister, T. J. *Mater. Sci. Forum* 1993, 113-115, 631. (c) Faust et al. *J. Phys. Chem. Solids* 1964, 25, 1407.
(20) Gleiter et al. *Philos. Mag.* 1973, 27, 1009.
(21) Liu et al. *Chem. Commun.* 2014, 50, 1804.
(22) (a) Gao et al. *J. Chem. Phys.* 2011, 134, 134702. (b) Neumann et al. *ACS nano* 2013, 7, 42.
(23) (a) Polman, A. *ACS nano* 2013, 7, 15. (b) Fang et al. *Nano Lett.* 2013, 13, 1736.
(24) (a) Sau et al. *J. Am. Chem. Soc.* 2004, 126, 8648. (b) Chen et al. *Langmuir* 2008, 24, 5233.

What is claimed is:

1. A method comprising:
reacting metallic nanorods in the presence of at least one solvent, at least one metal precursor, at least one organic ligand, and at least one reducing agent in effective amounts and reaction conditions,
wherein the effective amounts and reaction conditions result in an asymmetric monometallic nanorod-nanoparticle dimer reaction product, with the nanorod and the nanoparticle of the dimer reaction product intergrown through metallic bonding.

2. The method of claim 1, wherein the metallic nanorods are gold nanorods, the solvent is water, the metal precursor is a gold metal precursor, and the organic ligand is a thiol ligand.

3. The method of claim 2, wherein the concentration of the thiol ligand is at least 10 mM.

4. The method of claim 3, wherein the thiol ligand is thiol mercaptophenol.

5. The method of claim 1, wherein the nanoparticle of the dimer reaction product has a lateral dimension size of about 10 nm to about 50 nm.

6. The method of claim 1 comprising:
reacting gold nanorods in the presence of effective amounts of at least one solvent, at least one gold metal precursor, at least one organic ligand, and at least one reducing agent,
Wherein the amounts and reaction conditions result in an asymmetric monometallic gold nanorod-nanoparticle dimer reaction product, with the gold nanorod and nanoparticle of the dimer reaction product intergrown through metallic bonding.

7. An asymmetric monometallic gold nanorod-nanoparticle dimer prepared by the method of claim 6.

8. The method of claim 1, wherein the reducing agent is ascorbic acid.

9. An asymmetric monometallic nanorod-nanoparticle dimer prepared by the method of claim 1.

10. The composition of claim 9, wherein the reducing agent is ascorbic acid, the reducing agent is ascorbic acid and the reaction condition comprises room temperature.

11. The method of claim 1, wherein the reaction condition comprises room temperature.

12. An asymmetric monometallic nanorod-nanoparticle dimer, wherein the nanorod and nanoparticle of the nanorod-nanoparticle dimer are connected through metallic bonding.

13. The dimer of claim 12, wherein the nanorod is a gold nanorod and the nanoparticle is a gold nanoparticle.

14. The dimer of claim 12, wherein the dimer is characterized by a strong absorption from about 300 nm to about 1,200 nm of at least 0.2 absorption units (a.u.).

15. A device comprising the dimer of claim 12.

16. The device of claim 15, wherein the device is a photovoltaic device, an amplifier for a random laser, a surface enhanced spectroscopic device, or a photothermo conversion device.

17. The composition 12, wherein the dimer comprises one nanorod.

* * * * *